United States Patent
Christensen et al.

(10) Patent No.: US 7,803,128 B2
(45) Date of Patent: Sep. 28, 2010

(54) NEEDLE INSERTION SENSOR

(75) Inventors: Lars Hofmann Christensen, Jyllinge (DK); Jens Ulrik Poulsen, Virum (DK); Jan H. Simonsen, Struer (DK)

(73) Assignee: Novo Nordisk A/S, Bagsvaerd (DK)

( * ) Notice: Subject to any disclaimer, the term of this patent is extended or adjusted under 35 U.S.C. 154(b) by 475 days.

(21) Appl. No.: 11/763,024

(22) Filed: Jun. 14, 2007

(65) Prior Publication Data

US 2007/0239133 A1    Oct. 11, 2007

Related U.S. Application Data

(63) Continuation of application No. 10/425,813, filed on Apr. 29, 2003, now abandoned.

(60) Provisional application No. 60/389,104, filed on Jun. 4, 2002.

(30) Foreign Application Priority Data

Apr. 30, 2002    (DK) ............................... 2002 00650

(51) Int. Cl.
    *A61M 31/00*    (2006.01)
(52) U.S. Cl. ...................................... 604/65
(58) Field of Classification Search ............. 604/65–67, 604/890.1, 131; 128/DIG. 12, DIG. 13
    See application file for complete search history.

(56) References Cited

U.S. PATENT DOCUMENTS

| | | | |
|---|---|---|---|
| 4,871,351 A | 10/1989 | Feingold | 604/66 |
| 5,113,869 A | 5/1992 | Nappholz et al. | 600/508 |
| 5,741,211 A | 4/1998 | Renirie et al. | 600/300 |
| 5,971,963 A | 10/1999 | Choi | 604/177 |
| 6,558,351 B1 | 5/2003 | Steil et al. | 604/131 |
| 6,770,070 B1 | 8/2004 | Balbierz | 606/41 |
| 6,796,963 B2 * | 9/2004 | Carpenter et al. | 604/117 |
| 6,887,238 B2 | 5/2005 | Jahns et al. | 606/41 |
| 7,066,922 B2 * | 6/2006 | Angel et al. | 604/500 |

(Continued)

FOREIGN PATENT DOCUMENTS

EP          0 221 005        5/1987

(Continued)

OTHER PUBLICATIONS

Search Report issued in connection with counterpart Danish Application No. PA 2002 00650, mailed Mar. 18, 2003.

(Continued)

*Primary Examiner*—Manuel A Mendez
(74) *Attorney, Agent, or Firm*—Marc A. Began; Wesley A. Nicolas

(57) ABSTRACT

This invention relates to a doser comprising a syringe (2) with a needle (3) which extends beyond the doser (1), which comprises an engagement face (4) in the vicinity of the needle so that the engagement face rests against the surface of the tissue into which the needle is inserted. Detector means (5) are provided on said engagement face to sample signals on the skin of the patient. The invention further provides means (13) for receiving external information related to health monitoring of a patient. This provides a doser that may record heart rate, EKG, BGM and hypo-alarm administered medicine. The doser may further be arranged to calculate an appropriate dose of medication on the basis of a number of acquired inputs.

24 Claims, 2 Drawing Sheets

U.S. PATENT DOCUMENTS

2002/0002326 A1    1/2002    Causey, III et al. .......... 600/300

FOREIGN PATENT DOCUMENTS

| GB | 2 309 644 | 8/1997 |
|---|---|---|
| GB | 2309644 | 8/1997 |
| IN | 165367 | 3/1986 |
| WO | 00/32088 | 6/2000 |
| WO | WO 02/24257 | 3/2002 |

OTHER PUBLICATIONS

Search Report issued in connection with counterpart PCT Application No. PCT/DK03/00275, mailed Jul. 25, 2003.

International Preliminary Examination Report issued in connection with counterpart PCT Application No. PCT/DK03/00275, mailed May 21, 2004.

* cited by examiner

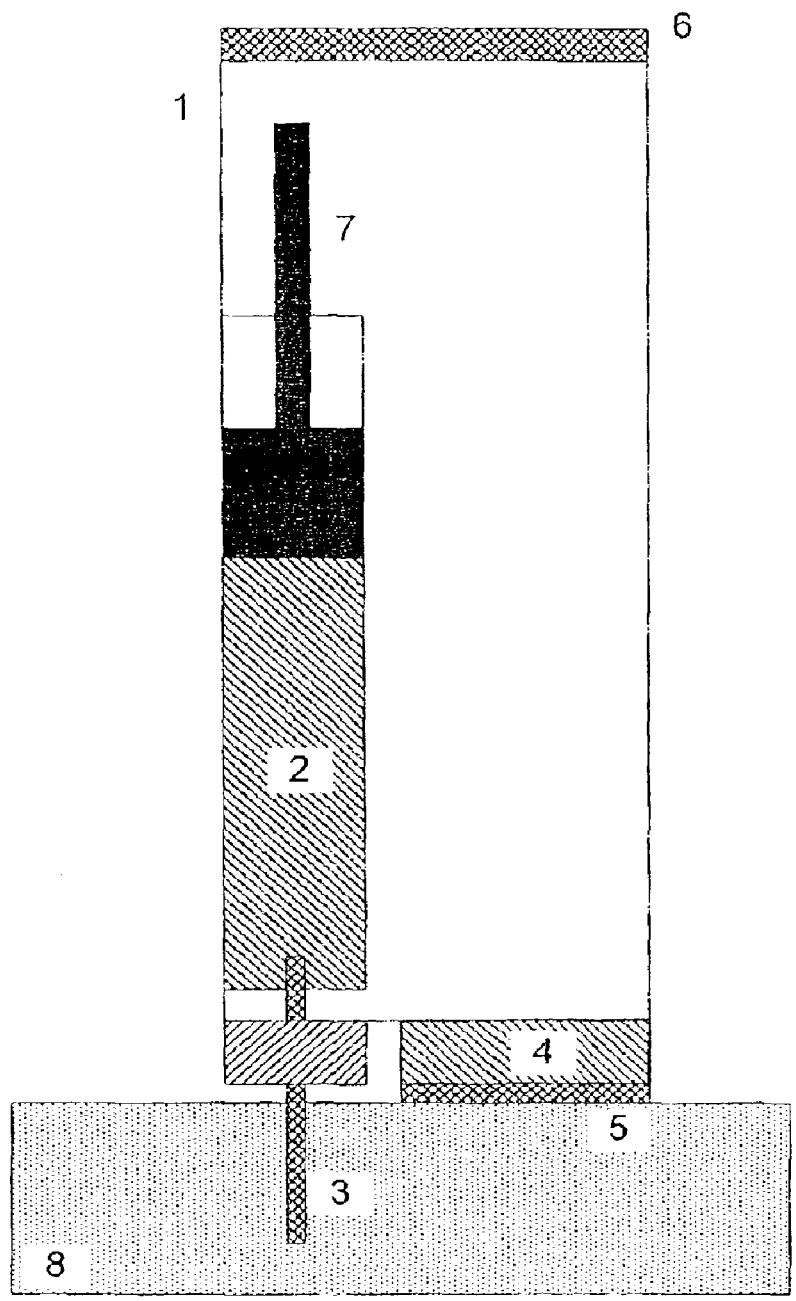
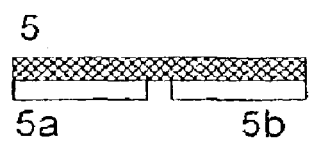

NEEDLE INSERTION SENSOR

CROSS-REFERENCE TO RELATED APPLICATIONS

This application is a continuation of U.S. application Ser. No. 10/425,813, filed Apr. 29, 2003, which claims priority under 35 U.S.C. 119 of Danish application PA 2002 00650 filed Apr. 30, 2002, and U.S. provisional application 60/389,104 filed Jun. 4, 2002, the contents of all of which are fully incorporated herein by reference.

FIELD OF THE INVENTION

The present invention relates to a doser comprising a syringe having a needle which extends outside the doser, which comprises an engagement face in the vicinity of the needle so that the engagement face rests against the tissue into which the injection is inserted.

BACKGROUND OF THE INVENTION

Injection devices for multiple use having an exchangeable insulin ampoule have been developed, which calculate an optimum dose of medicine for a given patient (WO 00/32088). This calculation can take the patient's health, food habits and recordings of previously administered doses into consideration. For this determination of dose it is necessary to know the patient's received dose precisely to avoid overdosing or underdosing, as this may have fatal consequences for the diabetic.

OBJECT OF THE INVENTION

The object of the invention is to utilize the known sophisticated electronics for even better information of the user on the basis of the provision of additional input signals to the electronics, without the user having to do anything else than he/she normally does.

This object is obtained in that measurements of the heart rate are accomplished in that signal processing known per se is used in combination with one or more electrode means for this measurement being provided on said engagement face.

Thereby signals are obtained that are related to heart activity and by expanding the doser with additional electrode means provided on the handle, it is possible to obtain electrocardiograms. Preferably additional electrode means are provided that can be located elsewhere on the body and, either via wires or wireless communication links, they are connected to the doser.

Preferably electrical signals are used, but it is also an option to use optical signals, like eg in connection with BGM measurements (Blood Glucose Measurement).

Typically, the impedance is measured in the tissue touched by the engagement face of the doser or, alternatively, light is used. The signals may be modulated to avoid noise from the surroundings.

An important feature of the invention is the finding that merely by a very simple detection of heart signals, it is possible to considerably improve the applicability. This is due to the fact that the prior art calculating circuits are very sophisticated, via with self-learning software routines that can either be executed within the doser as such or be executed in a large, external computer connected to the doser via a wire or a wireless communication link. In this manner the doser may have very large signal-processing capacity and therefore the doser can advantageously be provided with means for receiving external signals.

By the provision of extra electrode means at the end opposite that end of the doser which is in contact with the skin of the stomach of the user, it is accomplished that the patient's hand touches the additional electrode means, whereby the measurement will take place through the patient's heart region. It is therefore possible, by simple means, to considerably broaden the applicability. By supplementing with light detection it is also possible to perform a blood glucose measurement (BGM) in connection with the doser that thus also lends itself for use as hypoglycemia alarm.

A further advantageous use of the invention relates to administering of the dosis which is injected. It is assumed in the calculations that all the medicine discharged from the ampoule is administered to the patient. When replacing the reservoir it is essential to drain the injection doser needle as well as the syringe for any possible air, as this might fill the patient's veins. Consequently, the operator usually performs a first time shot e.g. into a sponge after reservoir replacement to make sure that there is no air left in the needle or eventual in the syringe. This shot will inappropriately be recorded in the doser as an injection shot into the patient, and it will therefore be necessary to observe whether the needle is inserted into biological tissue, e.g. a human body. This drawback is avoided by the doser according to the invention that can very reliably detect whether dosis is administered to biological tissue, since the decision can be taken on the basis of the detection of heart rate.

BRIEF DESCRIPTION OF THE DRAWINGS

The accompanying drawings illustrate the present invention by way of the embodiments in which:

FIG. 1 shows an embodiment of the doser according to the present invention where the engagement face rests against skin.

FIG. 3 shows an embodiment of a sensor with two electrodes according to the present invention.

DETAILED DESCRIPTION OF THE INVENTION

Figure 2:
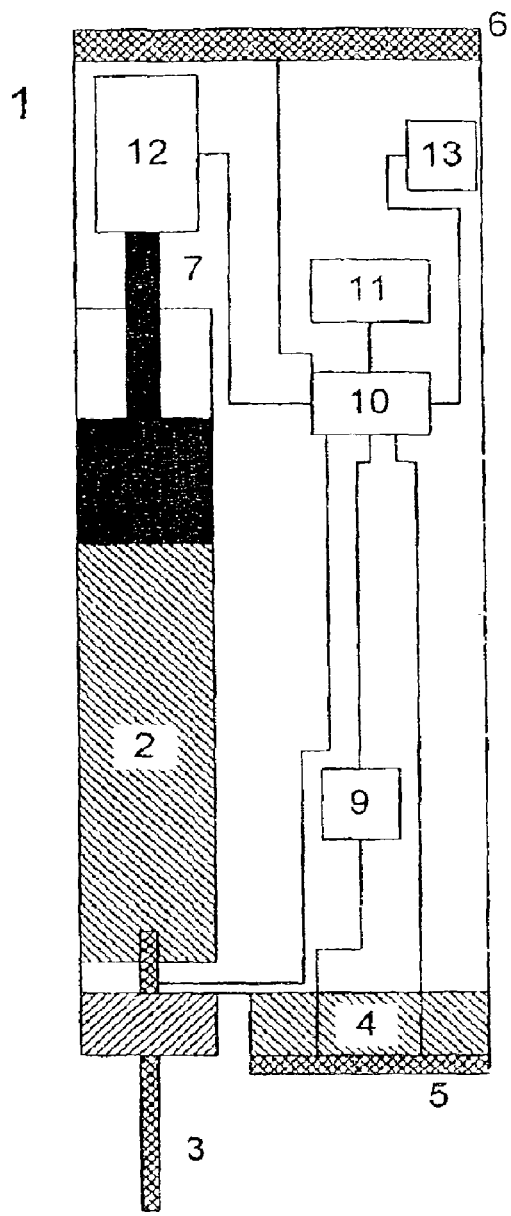
FIG. 2 illustrates an embodiment of the invention in detail and with sensor means on the injection button.
Figure 4:
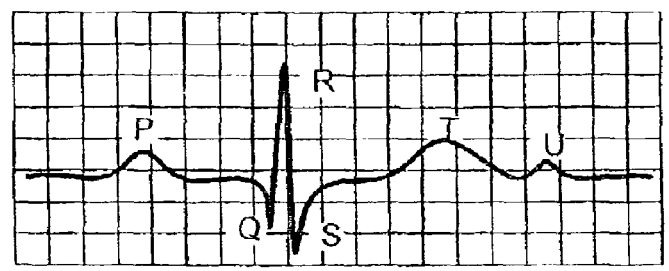
FIG. 4 illustrates a QRS-pass as seen on a typical electrocardiogram.

FIG. 1 shows detector means (5) on the engagement face (4) of a doser that naturally contacts the skin (8) in normal use.

The doser (1) comprises a syringe (2) having a needle (3) that generally extends outside the doser that comprises an engagement face (4) in the vicinity of the needle, so that the engagement face rests against the surface of the tissue (8) into which the needle has been inserted. The engagement face has one or more closely spaced electrodes connected to detector means for measuring electrical pulses.

FIG. 3 shows an example of such a sensor (5) with two closely spaced electrodes (5a, 5b).

In an embodiment, the electrical impedance between such two electrodes is measured, and it can hereby be determined whether the doser is in engagement with human tissue. The doser may thus be adapted for specifically recording the amount of administered dose to a tissue type having human characteristics.

According to the invention, the heart rate of the patient can be determined by a continuous recording of the impedance of the skin, which gives a further indication of live tissue not obtained in prior art whereby a more safe decision can be made to determine whether the insulin discharge takes place in a patient.

More importantly, the detector means according to the invention can be used to determine the heart rate itself, even if a person skilled in the art would expect that heart rate signals obtained in a way according to the invention—at least to a certain extent—would be of too low a quality to make a decision on something as important as the heart rate.

By combining the detector means according to the invention with modern signal shaping routines, e.g. comprising naural network analysis (see WO 02/069798) reliable results can be obtained on the basis of less reliable detector signals whereby the invention is operable even under difficult conditions.

If the patient's skin is wet, the impedance between the electrodes of the engagement face will be measured so low that it is determined by the doser that human-like skin is not involved. In this case it is therefore expedient that the needle can comprise a sensor, e.g. an electrode, thereby allowing a measurement between the sensor of the engagement face (5) and the sensor of the needle. This provides an extra possibility of reliable measurement results.

In a preferred embodiment a sensor is embedded also in the handle of the doser (6). This allows for measurement between it and the sensor of the engagement face (5) and/or the sensor of the needle (3). According to the invention, this makes the heart rate signals useable for obtaining electrocardiogram signals, as will be described below.

Since an injection is typically made in the patient's thigh or pit of the stomach, the current path between the sensors of the doser at the end of the engagement face and the handle of the doser will run through the patient's heart region and one arm, which enables mapping of the heart rate as well as diastole and systole of the patient's ventricles. This possibility allows diagnosis of the patient's circulatory state, that is, if the patient himself operates the doser.

In this embodiment, the doser may moreover be adapted for calculating correlation between a sensor signal originating from the engagement face (5) and the sensor signal of the handle (6) so as to determine whether these pulse rates are consistent. If these two signals do not resemble each other, it will mean that the patient does not operate the apparatus himself, but that the apparatus is operated by another person, e.g. a nurse. The doser can thus determine on the basis of this correlation that it is not possible to create a valid pseudo electrocardiogram (ECG).

The basics of the doser according to the present invention are shown in FIG. 2. Signal processing/calculation means (10) is connected with memory storage (11) containing e.g. user information, operating system, executable program, etc.

The processing means may include a microprocessor, an application-specific integrated circuit, or another integrated circuit, a smart card, a general purpose computer adapted by suitable software, or the like. The processing means may be designed to acquire information from the internal sensors/electrodes (3, 5 and 6) as well as from an external communication link (13). The communication link (13) may be any transmission line which may comprise wire and wire-less communication links.

Additionally, the processing means may comprise means to control the generation of control signals to a pump (12), e.g. a DC-driven motor, etc., which may enable an injection by way of moving a piston rod (7) in the syringe (2). Further, a signal device (9) may be present to generate measurement impulses, e.g. a light emitter generator etc.

Creation of a standard ECG signal requires measurement on three points on the patient's body. Even though the number of acceptable sensor points in this embodiment will be three (handle, needle, and engagement face), this method will not always be sufficient to obtain a complete electrocardiogram. Since the needle and engagement face sensor points are spaced closely together, the measurement signal processing requires an unacceptable high signal/noise ratio. To overcome this, it is therefore desirable to ensure that at least one external sensor for this purpose can be connected to the doser. In this embodiment, it will thus be possible to generate a true balanced measuring signal. This connection may be carried out by a physical wire and/or radio communication. To screen noise from the surroundings, it is necessary strongly to filter the resulting signal of especially the 50/60 HZ power supply frequency. The signal may then be chased for a possible useful ECG signal where a QRS course is desired.

In this case, the doser is adapted to recognize the shape of the QRS course of a human heart. To achieve a better noise/signal ratio, the measuring signal may be modulated in frequency to a range, which is discordant relative to the frequency of the power supply, that is, at a frequency which is not a whole numbered multiple of the power supply frequency.

If freedom of movement is desired, this sensor may consist of a wireless electrode having a plurality of electrodes (U.S. Pat. No. 6,073,046) adhered to the patient's chest. By implementation of ECG monitoring by means of the doser, this can completely replace a commonly used ECG apparatus.

It is also to be understood that the communication link 13 can be used to transmit information about the heart rate signals measured to a separate computer. Especially when a neural network is used to enhance the quality of the signal as disclosed in WO 02/069798, it may be expedient to use an external computer with large processing power instead of building in an internal computer having limited processing power.

It is moreover possible to replace the electrodes by an emitter/detector or receiver/transducer so as to enable emission and reception of optical signals and ultrasonic signals, respectively.

The use of optical signals provides a new possibility for the field of use of the doser for measuring physiological parameters. For an effective treatment of diabetes, it is necessary to know the patient's content of glucose in the blood (called BGM below), since this quantity influences the determination of the insulin dose amount. Currently, much research is focused on intravenous measuring methods which can determine the BGM by means of optics (U.S. Pat. No. 6,043,492) or by means of electrochemical sensors (U.S. Pat. No. 5,954,685). These sensors measure on the patient's skin and therefore eliminate the need for invasion.

The use of such sensors in the doser allows these methods to be employed for carrying out glucometry during injection, without the patient noticing this or performing any other actions. When commencing an injection, the doser may record the BGM with a view to determining the insulin amount and/or recommending an optimum diet for the patient, as described in WO 00/32088.

Some times, however, the patient wants to check the glucose state before he/she decides on insulin injection. If the patient exclusively wants to know the BGM and therefore does not want to insert the needle into the body, it will be desirable that the doser is adapted to accommodate the entire needle so that the needle may be pushed/pulled into the doser, whereby the needle will be hidden at times when it is not needed. As long as the needle does not extend outside the doser, a measurement may be performed simply by keeping the doser with the engagement face against the skin. This simple measuring method will motivate the patient to check the BGM to a greater extent, which can contribute to a better controlled treatment and therefore fewer sufferings because of diabetes over a span of years.

In summary, when detector means are provided on a doser for detecting of heart rate, a lot of new features can be obtained. Obtaining partly or full-scale EKG signals and the option of BGM measurements have been described. It will be understood that these features could also be made use of for making a hand-held hypo-alarm.

The invention claimed is:

1. A method of determining the quantity of medication delivered from an injection device into biologic tissue comprising:
   a) determining whether a needle is inserted into biologic tissue and if the needle is inserted into biologic tissue, measuring and recording the amount of medication injected, wherein when the needle is not inserted into biologic tissue, the amount of medication expelled through the needle is not recorded; and
   b) repeating a) before medication is injected through the needle and summing the amount of medication injected through the needle into biologic tissue.

2. The method of claim 1, wherein the determining whether the needle is inserted into biologic tissue comprises recording changes in impedance to a circuit that is electrically connected to the needle.

3. The method of claim 2, wherein the impedance is measured by at least two sensors.

4. The method of claim 3, wherein the impedance is measured by at least one sensor connected to the needle, and at least one other sensor.

5. The method of claim 3, wherein at least one sensor which measures impedance comprises an electrode.

6. The method of claim 4, wherein the at least one sensor connected to the needle which measures impedance comprises an electrode.

7. The method of claim 4, wherein the at least one other sensor which measures impedance comprises an electrode.

8. The method of claim 1, wherein the medication is an insulin.

9. The doser according to claim 8, wherein the doser comprises an emitter for generating and emitting light and detector means for detecting light.

10. The doser according to claim 1, wherein the electrodes are sensitive to electrical signals.

11. The doser according to claim 1, wherein the electrodes are sensitive to optical signals.

12. A doser for determining the quantity of medication delivered from an injection device into biologic tissue, the doser comprising:

an injection device comprising a syringe with a needle, and an electrode, the injection device extending from the doser, an engagement face in the vicinity of the needle for engaging a surface of a tissue into which the needle is to be inserted, the engagement face comprising at least one additional electrode, wherein the electrodes are capable of detecting a physiological parameter in the tissue by generating electrical signals;

electrical circuits adapted to generate and receive electrical signals and configured to measure the impedance between electrodes, and determine whether a needle is inserted into biologic tissue, such that if the needle is inserted into biologic tissue, measuring and recording the amount of medication injected, and when the needle is not inserted into biologic tissue, the amount of medication expelled through the needle is not recorded, and summing and recording the amount of medication injected through the needle into biologic tissue, wherein the electrical circuits are adapted to determine the quantity of medication delivered from the injection device into biologic tissue.

13. The doser according to claim 12, wherein the signals are modulated.

14. The doser according to claim 12, wherein the electrical circuits comprise a calculating circuit and a storage circuit adapted to process and store the value of said signals.

15. The doser according to claim 12, wherein said engagement faces are positioned at one end of the doser, characterized in that the additional electrode means are arranged at the opposite end of the doser.

16. The doser according to claim 12, wherein said electrodes comprise a pair of mutually closely spaced electrodes.

17. The doser according to claim 16, wherein the doser is adapted to estimate electrocardiogram signals.

18. The doser according to claim 12, wherein the circuits are adapted to recognize specific signal shapes.

19. The doser according to claim 12, wherein the circuits are adapted to determine pulse rates.

20. The doser according to claim 12, wherein the circuits is adapted to calculate the blood glucose level.

21. The doser according to claim 20, wherein the circuits are adapted to calculate doses in dependence on the calculated blood glucose level.

22. The doser according to claim 21, wherein the circuits are adapted to control the generation of control signals to a pump in the doser.

23. The doser according to claim 12, wherein the doser is structured to receive external signals, and that the circuit in the doser is adapted to combine the external signals with signals from the detector.

24. The doser according to claim 23, wherein the doser is structured for wireless communication.

* * * * *